United States Patent [19]

Žmitek et al.

[11] Patent Number: 5,498,788
[45] Date of Patent: Mar. 12, 1996

[54] INCLUSION COMPLEXES OF CLAVULANIC ACID AND OF POTASSIUM SALTS THEREOF WITH HYDROPHOBIC β-CYCLODEXTRIN DERIVATIVES A PROCESS FOR THE PREPARATION THEREOF

[75] Inventors: Janko Žmitek; Darja Ferčej-Temeljotov, both of Ljubljana; Katarina Verhnjak, Ptuj; Sonja Kotnik; Mateja Kovačič, both of Ljubljana, all of Slovenia

[73] Assignee: LEK, tovarna farmacevtskih, Slovenia

[21] Appl. No.: 369,301

[22] Filed: Jan. 6, 1995

Related U.S. Application Data

[63] Continuation of Ser. No. 84,951, Jul. 2, 1993, abandoned.

[30] Foreign Application Priority Data

Jul. 8, 1992 [SI] Slovenia ............... P-9200139

[51] Int. Cl.$^6$ .................. C07D 487/04; A01K 9/26
[52] U.S. Cl. .................. 540/349; 424/470; 536/103
[58] Field of Search ................ 424/490; 540/349

[56] References Cited

U.S. PATENT DOCUMENTS

| | | | |
|---|---|---|---|
| 4,454,069 | 6/1984 | Cook et al. | 260/245.3 |
| 4,525,353 | 6/1985 | Cole et al. | 424/114 |
| 4,647,659 | 3/1987 | Cook et al. | 260/349 |
| 4,869,904 | 9/1989 | Uekama et al. | 424/400 |
| 5,310,898 | 5/1994 | Copar | 540/349 |

FOREIGN PATENT DOCUMENTS 1508977  4/1978  United Kingdom .

OTHER PUBLICATIONS

Lenga, Robert, The Sigma–Aldrich Library of Chemical Safety Data, Edition 1, 1985, p. 310.
Bekers, et al., Cyclodextrins in the Pharmaceutical Field, Drug Development and Industrial Pharmacy, vol. 17, No. 11 (1991), pp. 1503–1549.

Chemical Abstracts, The American Chemical Society, vol. 101, No. 21 (1984), p. 808.

Hedges, Allan, Minutes of the Sixth International Symposium on Cyclodextrins, Symposium organized by American Maize–Products Company, (1992) pp. 1–8.

Matsubara, et al., Possible Use of Triacetylated Cyclodextrins in the Preparation of Sustained–Release Oily Injection of LHRH Agonist, Buserelin Acetate, pp. 547–550.

Karuzomi et al in Chem. Pharm. Bull vol. 23, pp. 3062–3068 (1975).

*Primary Examiner*—Jyothsna Venkat
*Attorney, Agent, or Firm*—Pollock, Vande Sande & Priddy

[57] ABSTRACT

Described is a new process for the preparation of alkali clavulanate from an aqueous solution of pure clavulanic acid and of pharmaceutically acceptable potassium crude clavulanic acid, which is obtained in a conventional manner after the fermentation with a clavulanic-acid-producing microorganism, extracted with an ethyl acetate solution of a hydrophobic β-CD derivative such as heptakis-(2,3,6-tri-O-acetyl)-β-CD in equimolar amount or up to 10% excess with regard to clavulanic acid. The resulting novel inclusion complexes of clavulanic acid and hydrophobic β-CD derivative in a molar ratio about 1:1 are isolated, purified with water and then converted with potassium 2-ethyl hexanate to the potassium clavulanate, which is isolated. Furthermore, there are described new inclusion complexes of clavulanic acid and of its pharmaceutically acceptable potassium salt both with hydrophilic β-CD derivatives and with hydrophobic β-CD derivatives, processes for the preparation thereof and the use thereof for the preparation of galenic forms with immediate as well as with sustained action, in combination with amoxicillin trihydrate, which are valuable medicaments in the therapy of infectious diseases.

6 Claims, 9 Drawing Sheets

INCLUSION COMPLEXES OF CLAVULANIC ACID AND OF POTASSIUM SALTS THEREOF WITH HYDROPHOBIC β-CYCLODEXTRIN DERIVATIVES A PROCESS FOR THE PREPARATION THEREOF

This application is a continuation of Ser. No. 08/084,951 filed on Jul. 2, 1993 now abandoned.

TECHNICAL FIELD

The present invention belongs to the field of pharmaceutical industry and relates to novel inclusion complexes of clavulanic acid and of potassium salt thereof, such as potassium or sodium clavulanate, with hydrophilic or hydrophobic β-cyclodextrin (abbr. β-CD for β-cyclodextrin), to the preparation thereof and to the use thereof as intermediate compounds the isolation of pure clavulanic acid or of alkali salts thereof from water solutions of crude clavulanic acid obtained in a known manner after the fermentation by a microorganism producing clavulanic acid as well as to the use thereof for the preparation of new stable galenic forms with immediate as well as sustained release.

TECHNICAL PROBLEM

There exists a constant need for a new and simple process for the preparation of pure clavulanic acid and of pharmaceutically acceptable potassium salt thereof whereby the desired compound with a high total yield and a high purity would be isolated from aqueous solutions obtained in a usual manner after the fermentation by a microorganism producing clavulanic acid.

Furthermore, there existed a need for new stable galenic forms of clavulanic acid or potassium clavulanate, with β-lactam penicillinic or cephalosporinic antibiotics such as amoxicillin trihydrate or ticarcillin, wherein the clavulanic acid or potassium clavulanate would have an improved stability in an acidic medium existing in the gastric mucuous membrane, which would result in an improved relative biological applicability of the active component.

PRIOR ART

Clavulanic acid is the generic name for (2R,5R,Z)-3-(2-hydroxyethylidene)-7-oxo-4-oxa-1-azabicyclo[3.2.0]heptane-2-carboxylic acid, which is a known compound of the following formula:

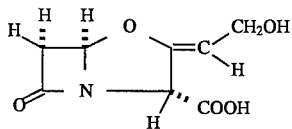

Alkali salts and esters thereof are active as inhibitors of β-lactamases, i.e. they inhibit the action of β-lactamases produced by some gram-positive and gram-negative microorganisms.

In addition to being inhibitors of β-lactamases, clavulanic acid or its alkali salts also have a synergistic effect in combination with β-lactam antibiotics of penicillinic and cephalosporin class, therefore clavulanic acid or alkali salts thereof are used in galenic preparations to prevent a deactivation of β-lactam antibiotics.

In the literature, there is described the possibility of clavulanic acid production in a fermentative manner by means of various mocroorganisms of the strain Streptomyces such as *S. clavuligerus* NRRL 3585, *S. jumoninensis* NRRL 5741, *S. katsurahamanus* IFO 13716 and Streptomyces sp. P6621 FERM P 2804.

Clavulanic acid and its alkali salts were first described in GB 1,508,977. After the fermentation by means of the strain *S. clavuligerus* NRRL 3585, the process for the isolation of clavulanic acid from the fermentation broth, which is based on the use of anionic exchange resins and exacting purifications by chromatographic methods, is time-consuming.

In GB patent 1,543,563 a modified fermentation process using the strain *S. clavuligerus* NRRL 3685 is described, whereat the pH value of the medium is maintained in a range between 6.3 and 6.7, whereby the yield of desired compound is increased. Clavulanic acid salts such as potassium clavulanate are prepared by resalting from lithium clavulanate.

An improved process for the isolation and purification of clavulanic acid and of its alkali salts is described in EP patent 0026044. This process is based on the preparation of an intermediate salt of clavulanic acid with tert. butylamine, preferably in the form of its acetone solvate, which is prepared by treating the extract such as ethyl acetate extract, which was prepared according to the process in GB patent 1,508,977, containing impure clavulanic acid and which was previously discoloured by treating with activated charcoal, with tert. butylamine in an organic solvent, followed by the conversion of the acetone solvate of the salt of clavulanic acid with tert. butylamine, which was previously also additionally purified by the recrystallization, with alkali carbonates, bicarbonates, hydroxides or salts of alkanoic acid such as potassium 2-ethylhexanoate, to the pharmaceutically acceptable alkali salts of clavulanic acid such as potassium clavulanate.

TECHNICAL SOLUTION

This invention is based on the task to isolate clavulanic acid or pharmaceutically acceptable potassium clavulanate, from concentrated aqueous solutions, which are obtained in the usual manner after the fermentation with a clavulanic-acid-producing microorganism, wherein clavulanic acid is present in a crude form, in a new, rapid and simple manner, whereby the desired compound would be obtained in an excellent total yield and with high purity. This aim was achieved so that a aqueous solution of crude clavulanic acid in the form of sodium salt was acidified with sulfuric acid to a pH value between 1 and 3, whereupon the acidified aqueous solution of crude clavulanic acid was immediately converted with a solution of a β-cyclodextrin hydrophobic derivative in an inert organic solvent such as ethyl acetate, to the inclusion complex of clavulanic acid with the β-cyclodextrin hydrophobic derivative, which was isolated from organic phase, which complex was purified with water and reacted with potassium 2-ethyl-hexanoate in an inert organic solvent such as ispropanol or acetone to the potassium clavulanate, which was then isolated.

Figure 1:
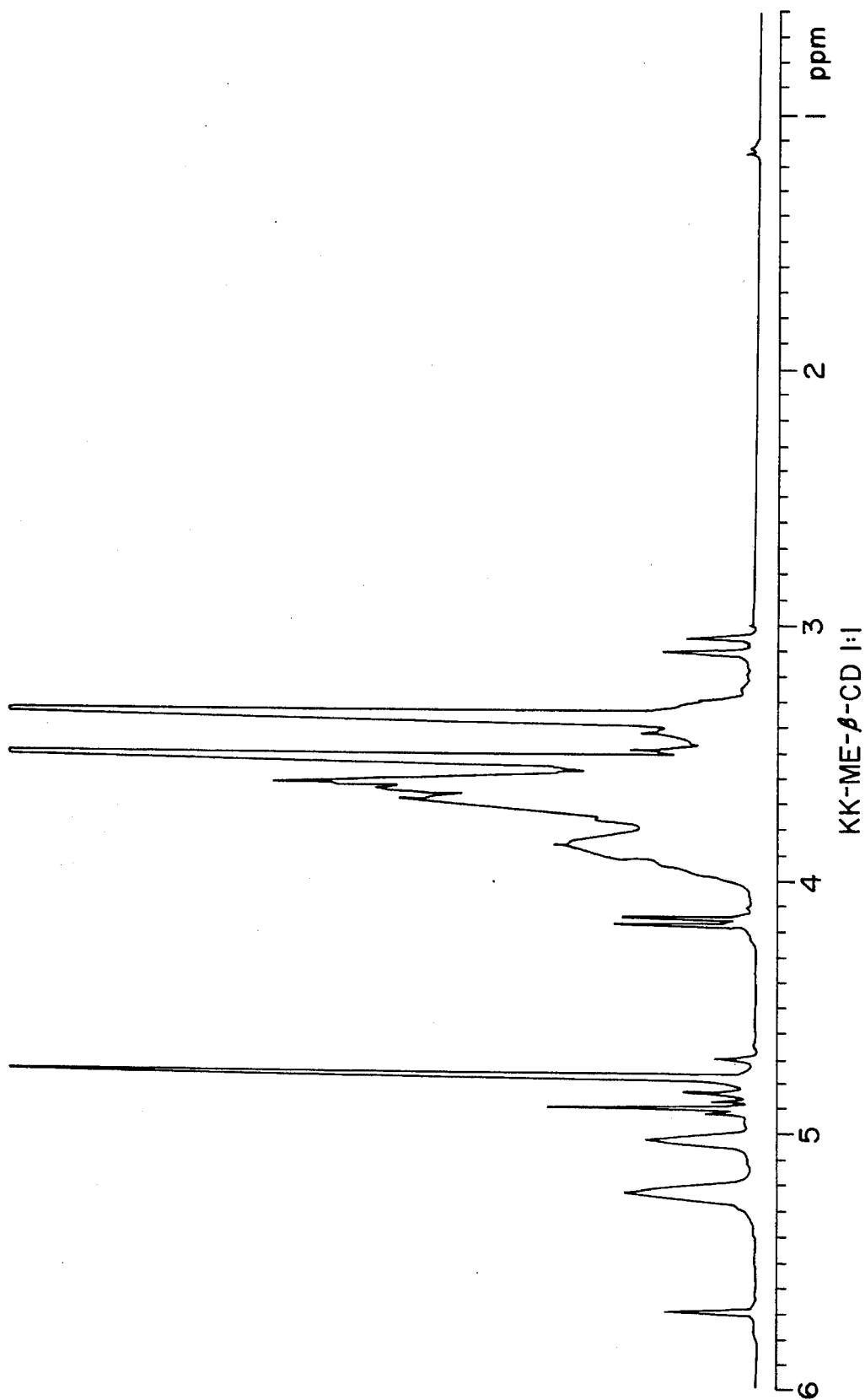
FIGS. 1 and 2 illustrate ¹NMR and DSC spectra'respectively, of inclusion complex of potassium clavulanate with methyl-β-cyclodextrin.

According to the invention, the aqueous solution (purified concentrate after fermentation) contained from 10 to 20 mg/ml of clavulanic acid in the form of its sodium salt (determined by the HPLC).

The conversion of the acidified water solution of crude clavulanic acid with the solution of β-CD hydrophobic derivative was carried out in an inert organic solvent such as ethyl acetate. With regard to the concentration of clavulanic acid, which was previously determined by the HPLC, an equimolar amount or excess (up to 10%) of β-CD hydrophobic dervative was used. The volume of the used inert organic solvent was about three times greater than the volume of the water phase. The obtained inclusion complex was very stable in an acidic medium, which also affected the high yield of the conversion.

As the β-cyclodextrin hydrophobic derivatives there were used: heptakis-(2,3,6-tri-O-acetyl)-β-CD (also abbr. as triacetyl-β-CD), in the nomenclature CAS (Chemical Abstracts Service) [23739-88-0] called β-cyclodextrin heneicosa acetate (the literature also reports abbr. TA-β-CD), heptakis-(2,6-di-O-ethyl)-β-CD (abbr. DE-β-CD), heptakis-(2,3-di-O-ethyl)-β-CD, heptakis-(2,3,6-tri-O-ethyl)-β-CD (abbr. TE-β-CD), O-carboxymethyl-O-ethyl-β-CD, heptakis-2,6-di-O-pentyl-β-CD, heptakis-2,3,6-tri-O-pentyl-β-CD, heptakis-(3-O-acetyl-2,6-di-O-pentyl)-β-CD, etc.

A short review of cyclodextrins is reported by O. Bekers et al.in Drug Development and Industrial Pharmacy, 17(11), 1503–1549 (1991), "Cyclodextrins in the pharmaceutical Field", wherein single cyclodextrin derivatives, terms or abbreviations, processes for the preparation of inclusion complexes, their characterization, the importance in pharmacy, etc. are described.

Hydrophobic β-CD are very poorly soluble in water. For example, the solubility in water of diethyl-β-CD is $5.0 \times 10^{-3}$ g/100 ml of water, and the solubility of triethyl-β-CD is $1.8 \times 10^{-3}$ g/100 ml of water.

Clavulanic acid itself or alkali salts therof are hydrophilic compounds that are very well soluble in water.

Inclusion complexes of clavulanic acid with β-CD hydrophobic dervatives such as the inclusion complex of clavulanic acid with heptakis-2,3,6-tri-O-acetyl-β-CD, which are formed in this step, are novel compounds, not yet described in the literature.

The obtained inclusion complexes are then isolated and, if desired, also purified, most conveniently by washing with water. The yield in this step is very high and amounts to over 90%. In comparison with the process for the isolation of clavulanic acid from ethyl acetate extract prepared in known manners and containing crude clavulanic acid, which is carried out via intermediate salts of clavulanic acid with tert. butylamine as described in EP 0026044, the process of the invention is advantageous because clavulanic acid bound in an inclusion complex such as the complex with triacetyl-β-CD, is significantly more stable at isolation conditions (low pH) than in the noncomplexed form (the complexation is selective for clavulanic acid). The separation of the water phase from the organic phase containing inclusion complex of clavulanic acid with TA-β-CD is made easier. Due to its stability, the inclusion complex can be saved for a longer period of time (some weeks), if necessary. Since the complex is crystalline and water-insoluble, it can be purified simply by washing with water to eliminate the water-soluble accompanying substances.

The intermediate inclusion complex of clavulanic acid with hydrophobic derivative of β-CD such as triacetyl-β-CD, is then reacted with potassium 2-ethyl-hexanoate, in an inert organic solvent such as isopropanol, whereby the potassium clavulanate is separated and then isolated.

All steps of the conversion are carried out at about ambient temperature.

The last step of conversion is also carried out easily and rapidly, whereat in a solution of an inert organic solvent such as isopropanol or acetone, the inclusion complex of clavulanic acid with triacetyl- β-CD is decomposed by the addition of alkali 2-ethylhexanoate in the same solvent, and the potassium clavulanate such as potassium clavulanate is separated.

Though in the step of the preparation of the intermediate complex there are required greater amounts of triacetyl-β-CD, which is added in at least equimolar ratio with regard to clavulanic acid (the molecular weight of a triacethyl-β-CD is about 10 times greater than the molecular weight of clavulanic acid), the used β-CD hydrophobic derivative can, after the isolation of the alkali clavulanate from the organic solvent solution, easily be recycled and returned back to the process.

A variant process for the isolation of potassium clavulanate from concentrated water solutions after the fermentation with a clavulanic-acid-producing microorganism is based on the conversion of the inclusion complex of clavulanic acid with triacetyl-β-CD, prepared in the above mentioned manner, with N,N'-diisopropylethylenediamine, whereat the obtained N,N'-diisopropilethylenediammonium diclavulanate is converted to the desired compound in the manner described in our Slovenian patent application SI P-92 00 392 and its corresponding U.S. Pat. No. 5,310,898.

This variant process is applied if a very high purity of the desired compound is required or in the cases when after fermentation the concentrated water solutions of clavulanic acid are not sufficiently pure.

The use of β-CD hydrophobic derivatives for the isolation of therapeutically effective active component such as clavulanic acid or potassium salt thereof from an aqueous solution of crude clavulanic acid, which is obtained in a conventional manner after the fermentation with a clavulanic acid producing microorganism is a new and nonobvious process not yet described in the literature and, in addition, these complexes are useful for the preparation of galenic forms with controlled release of the active component since the inclusion complex is retardative by itself.

A further object of the invention is the preparation of inclusion complexes of potassium clavulanate with β-CD hydrophilic derivatives and their use in the preparation of stable galenic forms for oral application such as capsules or tablets (effervescent, dispersive, chewing etc.) containing, in addition to the pharmaceutically acceptable carrier, a therapeutically effective amount of amoxicillin trihydrate and potassium salt of clavulanic acid, whereat the weight ratio between amoxicillin trihydrate and equivalent of potassium clavulanate bound in the complex amounts from 10:1 to 1:1.

From GB patent 2,005,538, there are known solid galenic forms containing, in addition to the pharmaceutically acceptable carrier, amoxicillin trihydrate and potassium clavulanate, whereat the preferred ratio of amoxicillin trihydrate and potassium clavulanate is 2:1. The recommended dose (in paediatrics) contains 250 mg of amoxicillin (in trihydrate form) and 125 mg of clavulanic acid (in potassium salt form). The recommended ratio of the components for adult patients is 4:1. Solid galenic forms such as capsules and tablets, which are described in this patent, have an improved stability. They are prepared in conditions of low-relative humidity (less than 30%) and the package also contains a drying agent such as silicagel because of the high hygroscopicity of clavulanic acid or potassium salt thereof.

The inclusion complexes of clavulanic acid or of potassium clavulanate, with β-CD hydrophilic derivatives of the invention may be prepared by known processes which are described in the literature, e.g. by M. Kurozumi et al., Chem. Pharm. Bull. 23(12), 3062–3068 (1975) or Acta Pharm. Technol. 36(1), 1–6 (1990), i.e. by complexing of active component with selected cyclodextrin, or they may be prepared in a novel manner, not yet described in the literature, which is a further object of the present invention.

According to the invention, the inclusion complex of clavulanic acid is reacted with hydrophobic β-CD such as triacetyl β-CD, which is obtained in the above-mentioned manner, in a water solution of an alkali base such as alkali carbonate, bicarbonate, hydroxide or alkanoate such as potassium 2-ethylhexanoate, directly with β-CB desired. This process representing substantially a recomplexing of one inclusion complex to another is, with regard to the aim of the invention, shorter than the above-mentioned one since no previous preparation of alkali cavalunate is necessary.

As β-CD hydrophilic derivatives there may be used all known compounds of this kind such as heptakis-(2,6-di-O-methyl)-β-CD, monomethyl-β-CD (Me-β-CD), heptakis-(2,3,6-tri-O-methyl)-β-CD, hydroxypropyl-β-CD, hydroxyethyl-β-CD, dihydroxypropyl-β-CD, β-CD branched derivatives such as glucosyl-β-CD, maltosyl-β-CD, dimaltosyl-β-CD, diglucosyl-β-CD and other water soluble or hydrophilic derivatives of β-CD.

In a dose unit, galenic forms of the invention may contain, in addition to the pharmaceutically acceptable carrier and other adjuvants, the same amounts of amoxicillin trihydrate and of equivalent of potassium clavulanate in a complex as commercial preparations.

It was unexpectedly found that by complexing clavulanic acid or its potassium salt, the stability of clavulanic acid at pH 1.2 and the temperature of 37° C., i.e. in the acidic medium as it is present in gastric juice, is substantially improved, whereby the repeating in the extent of the absorption of clavulanic acid from the gastrointestinal tract or the biological availability of the active component is improved.

The stability of clavulanic acid itself in conditions being present in gastric juice is exceptionally low (the time of 95% decomposition of clavulanic acid at 37° C. is 26 minutes), whereas, due to the complexing of the clavulanic acid with β-CD, its acid stability is improved, which makes possible the absorption of clavulanic acid from the gastrointestinal tract to the blood in a greater extent, which is much less dependent on the pH of the medium (as in the gastric mucuous membrane). This further contributes to a greater therapeutical effectiveness in a combination with amoxicillin trihydrate since the inhibition of β-lactamases is increased. This certainly means that in order to achieve the same therapeutical effect as by a commercial preparation (Augmentin), lower doses of clavulanic acid or potassium clavulanate may be used.

A further object of the invention are inclusion complexes of clavulanic acid or of its potassium salt with β-CD hydrophobic derivatives such as heptakis-(2,3,6-tri-O-acetyl)-β-CD, which may be obtained by the above-mentioned process or may be prepared from both components in known manners which are described in the literature, which represent a sustained release system, wherefrom the active component is released in a controlled manner as shown in the graph. The inclusion complex itself represents a sustained release complex and therefore no other sustained release components in the galenic form are necessary. To galenic forms with a sustained release of the active component, in addition to the inclusion complex and amoxicillin trihydrate, adjuvants such as desintegrators, fillers, colouring agents, sweetening agents etc. may be added if necessary.

A further object of the invention is to prepare stable galenic forms with a controlled release of the active component, which contain amoxicillin trihydrate and a mixture of two inclusion complexes of clavulanic acid or of its potassium salt, whereat one of the β-cyclodextrin derivatives used for complexing is hydrophilic and the other is hydrophobic.

In this case the release of active component from the galenic form may be controlled in the desired extent by a suitably adapted ratio of the two types of inclusion complexes.

Owing to the high stability in the acidic medium of gastric juice and a suitable sustained rapidity of releasing clavulanic acid from the system, these complexes have an improved biological applicability.

All inclusion complexes of clavulanic acid and of its potassium salt with hydrophilic or hydrophobic β-CD derivatives according to the invention are formed in a molar ratio of about 1:1.

From U.S. Pat. No. 4,869,904, a sustained release system of inclusion complexes of the active components with β-CD hydrophobic alkylated derivatives such as heptakis-(2,3-di-O-ethyl)-β-CD is known.

According to the invention, in addition to the heptakis-(2,3,6-tri-O-acetyl)-β-CD also O-carboxymethyl-O-ethyl-β-CD, heptakis-2,6-di-O-pentyl-β-CD, heptakis-2,3,6-tri-O-pentyl-β-CD or heptakis-(3-O-acetyl-2,6-di-O-pentyl)-β-CD may be used as the hydrophobic β-CD derivative.

No toxic effect was observed in any of the performed tests. Thus it may be considered that the toxicity of the inclusion complexes is as low as the toxicity of clavulanic acid or its potassium salt.

The invention is illustrated but in no way limited by the following Examples.

EXAMPLE 1

Preparation of the inclusion complex of potassium clavulanate with methyl-β-cyclodextrin (Me-β-CD) Me-β-CD (13.10 g, 10 mmol) was dissolved in water for injections (25 ml) under stirring at ambient temperature and then to the solution potassium clavulanate (2.377 g, 10 mmol) was slowly added under constant stirring. The obtained solution was stirred at ambient temperature in the dark for 10 minutes, then it was filtered, the filtrate was frozen in a stream of liquid nitrogen and then it was freeze-dried.

There was obtained a slightly yellowish microcrystalline title complex (15.25 g, 98.5%). The complex contained 15.2% of potassium clavulanate as it was determined by the HPLC method.

Figure 2:
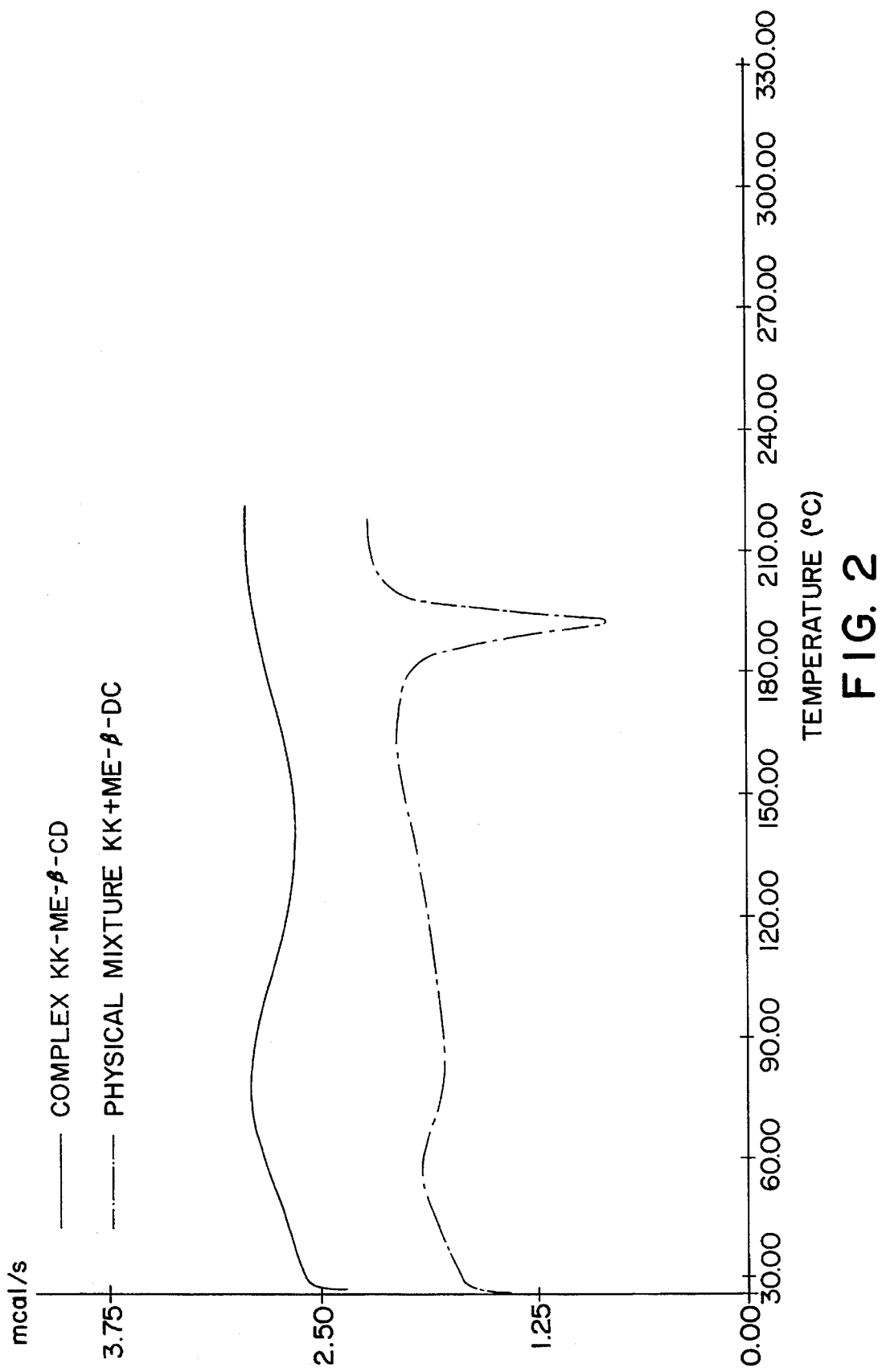

FIGS. 1 and 2 illustrate $^1$NMR and DSC (differential scanning calorimetry) spectra of the title complex.

EXAMPLE 2

Preparation of the inclusion complex of potassium clavulanate with 2-hydroxypropyl-β-CD (2-HP-β-CD)

It was proceeded in the same way as in Example 1, only that methyl-β-cyclodextrin was replaced by 2-hydroxypropyl-β-cyclodextrin (13.80 g, 10 mmol).

There was obtained a microcrystalline title complex (16.0 g, 99.3%). The complex contained 14.6% of potassium clavulanate as it was determined by the HPLC method.

Figure 3:
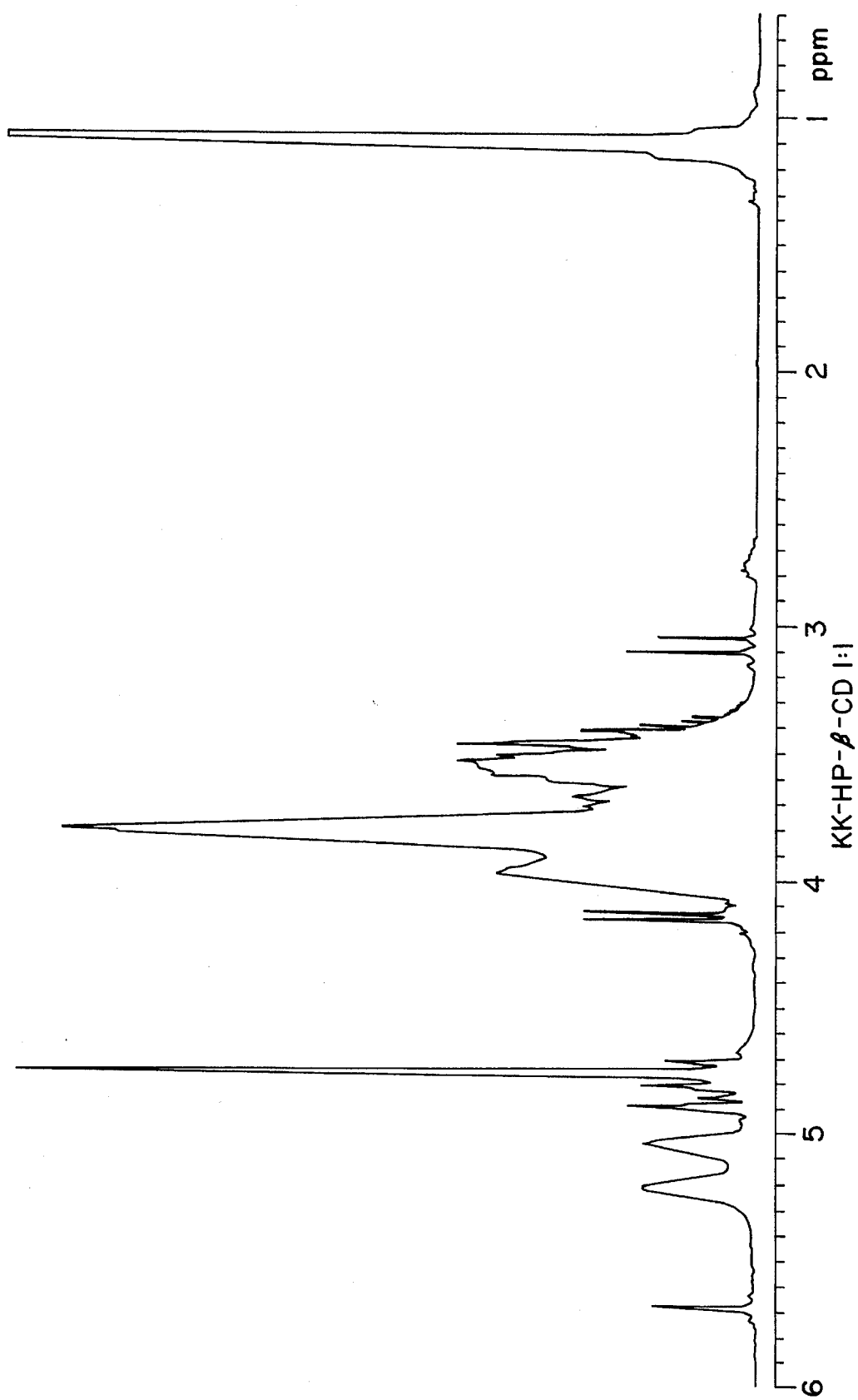
FIGS. 3 and 4 illustrate ¹NMR and DSC spectra, respectively, of inclusion complex of potassium clavulanate with 2-hydroxypropyl-β-cyclodextrin.
Figure 4:
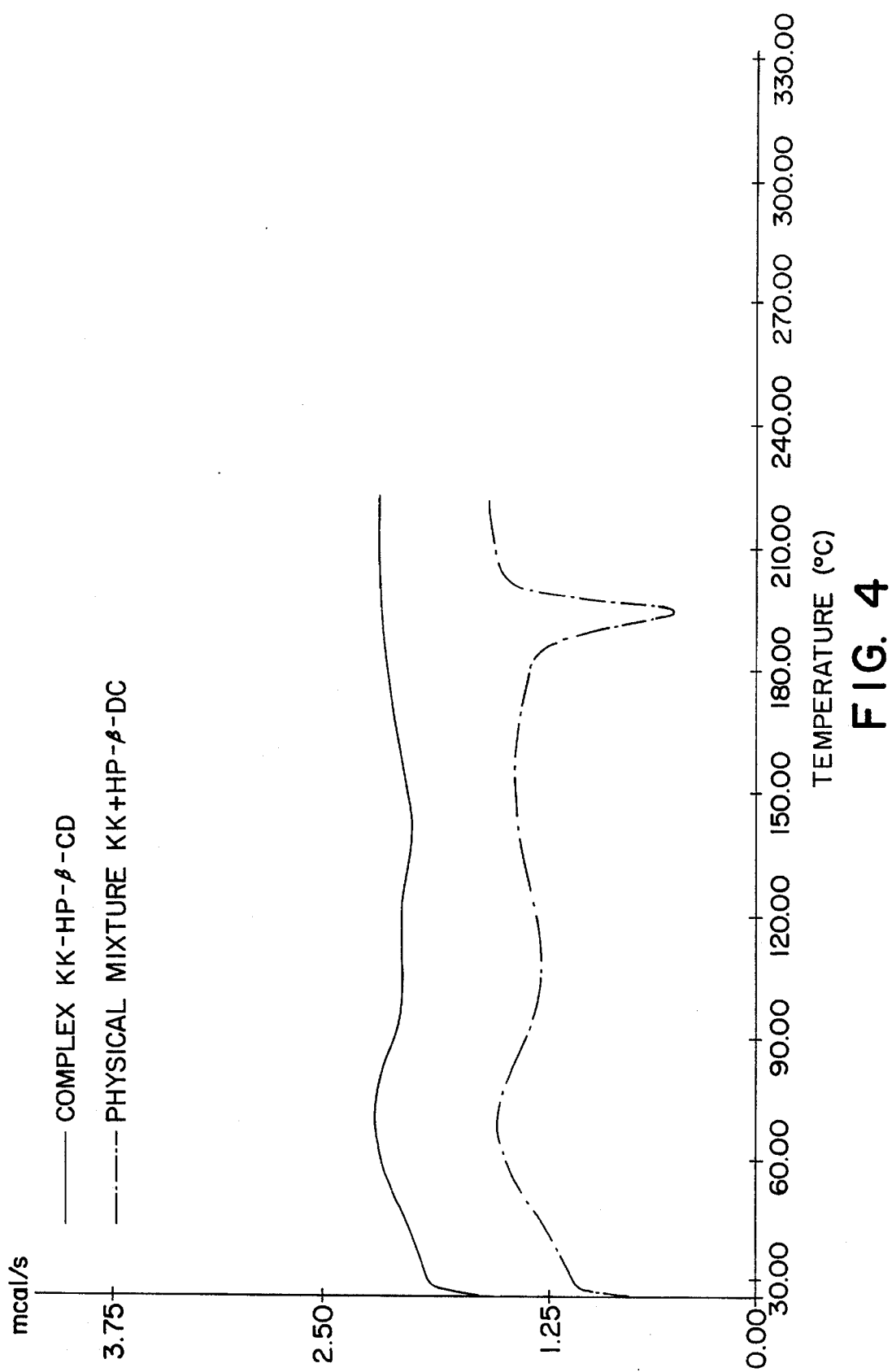

FIGS. 3 and 4 illustrate $^1$NMR and DSC spectra of the title complex.

EXAMPLE 3

Preparation of the inclusion complex of potassium clavulanate with 2-hydroxyethyl-β -cyclodextrin (2-HE-β-CD)

It was proceeded in the same way as in Example 1, only that methyl-β-cyclodextrin was replaced by 2-hydroxyethyl-β-CD (14.40 g, 10 mmol).

There was obtained microcrystalline title complex (16.2 g, 96.7%). The complex contained 13.9% of potassium clavulanate as it was determined by the HPLC method.

Figure 5:
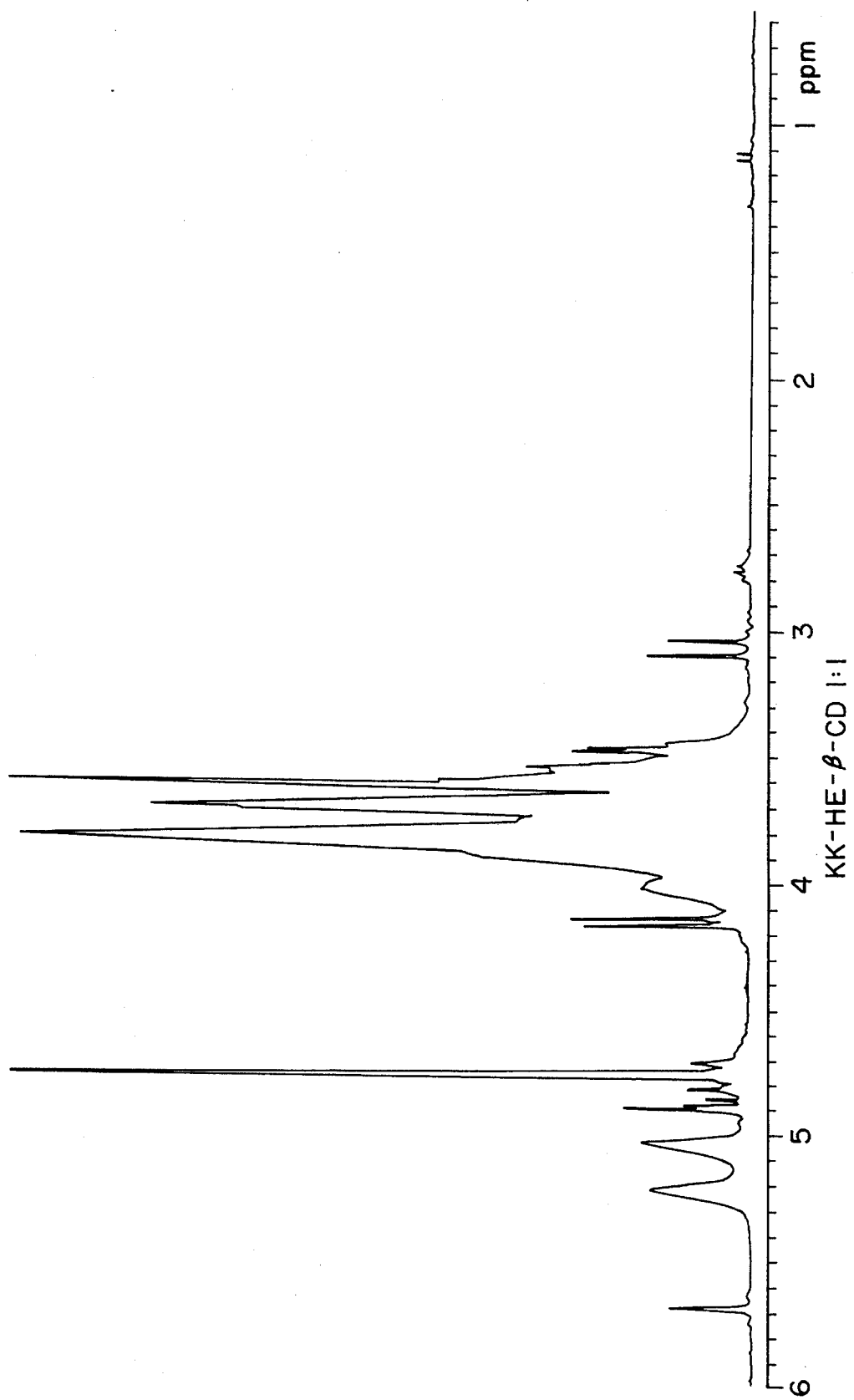
FIGS. 5 and 6 illustrate $^1$NMR and DSC spectra, respectively, of inclusion complex of potassium clavulanate with 2-hydroxyethyl-β-cyclodextrin.
Figure 6:
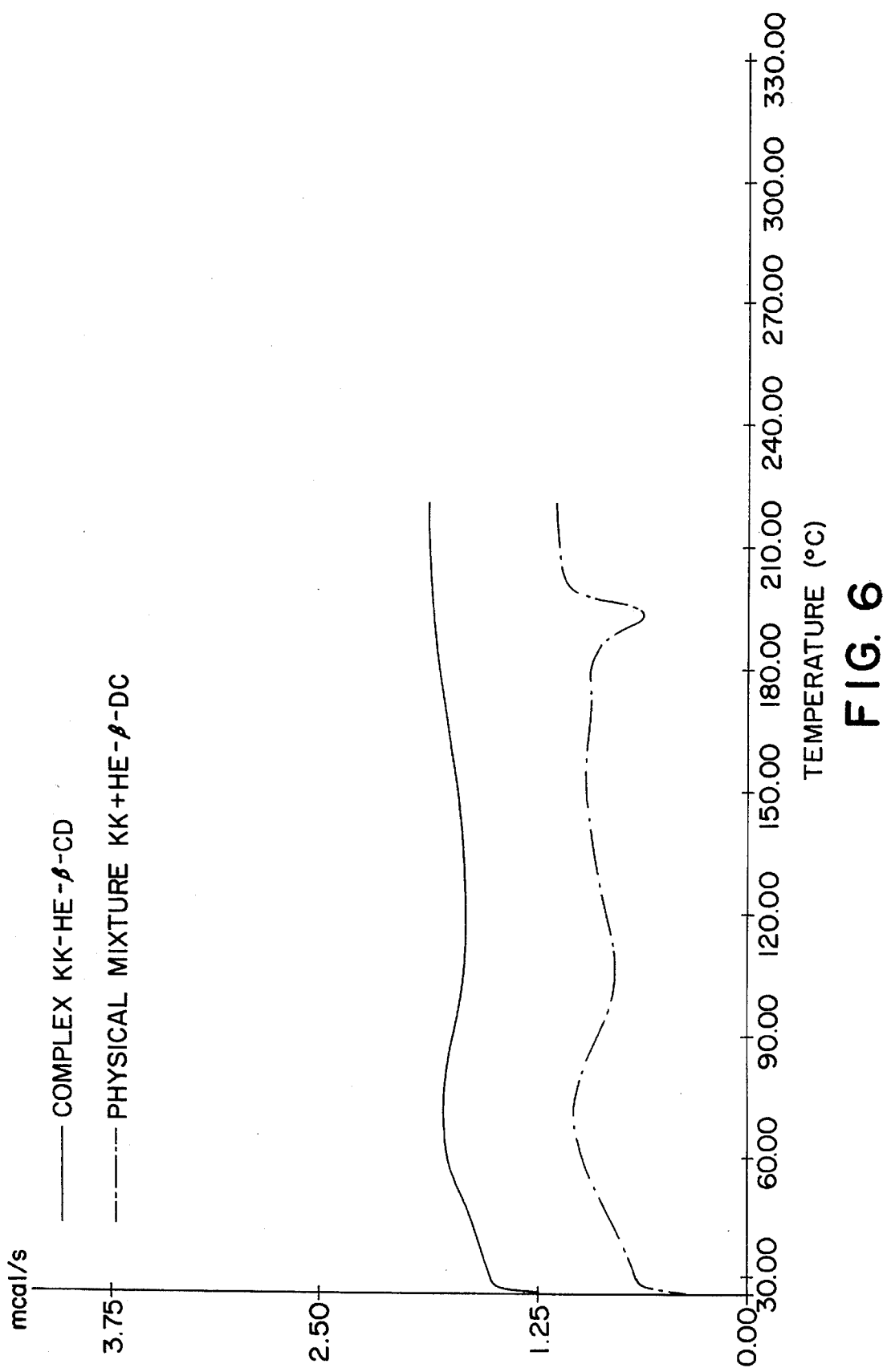

FIGS. 5 and 6 illustrate $^1$NMR and DSC spectra of the title complex.

EXAMPLE 4

Process for the isolation of clavulanic acid or of potassium salt thereof from an aqueous solution of crude clavulanic acid.

A water solution (1.25 l) containing clavulanic acid (20 g, 0.1 mol) was acidified with conc. sulfuric acid (15 ml) to the pH value of 1.3 and then the acidified water solution was immediately extracted in a centrifuge with ethyl acetate (4.0 l) in which heptakis-( 2,3,6-tri-O-acetyl)-β-CD (201.78 g, 0.1 mol) was dissolved. The phases were separated and the organic phase was washed with water (250 ml) on a separative column. Subsequently, the solvent was evaporated from the organic phase and the residue was dried in vacuum at the temperature of 35° C. to a constant weight. There was obtained a crude inclusion complex (212.9 g, 96%) of clavulanic acid with heptakis-(2,3,6-tri-O-acetyl)-β-CD, which was then digested in water (500 ml) under vigorous stirring. The complex was then filtered off, washed with water (3×50 ml) and dried in vacuum at a temperature up to 35° C. to the constant weight (210.4 g). The complex contained 8.1% of clavulanic acid as it was determined by the HPLC method.

The purified inclusion complex (210.4 g) of clavulanic acid with triacetyl-β-CD was dissolved in acetone (250 ml), the solid particles were filtered off and a solution (100 ml, 20%) of potassium 2-ethyl-hexanoate in isopropanol was slowly added dropwise under stirring. Potassium clavulanate separated and it was filtered off, washed with isopropanol (3×15 ml) and dried in vacuum at a temperature up to 35° C. to the constant weight. The yield of potassium clavulanate was 18.0 g (88 %) (the clavulanic acid content of 83.0 % was determined by the HPLC).

Figure 7:
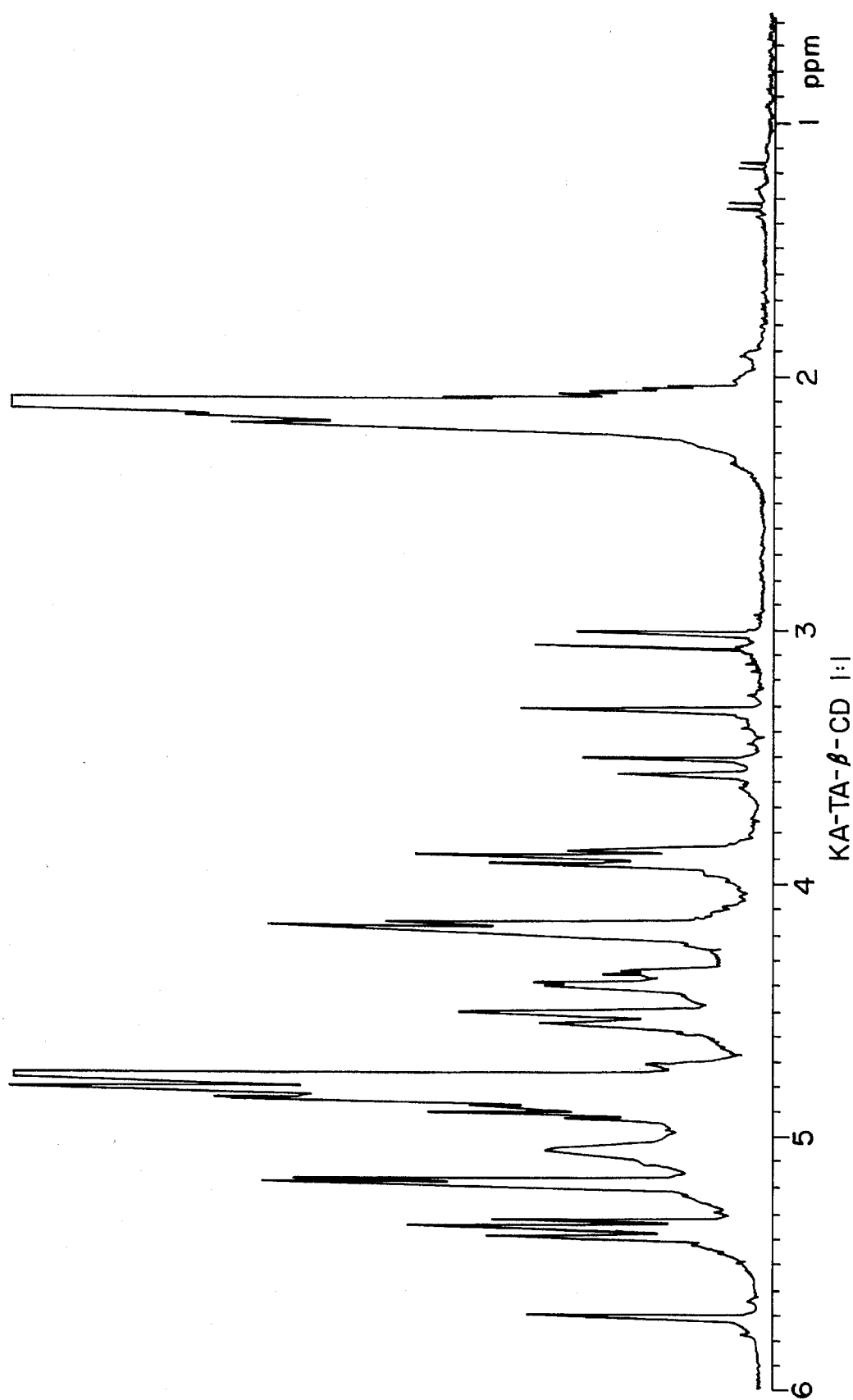
FIGS. 7 and 8 illustrate $^1$NMR and DSC spectra, respectively, of inclusion complex of clavulanic acid with triacetyl-β-cyclodextrin.
Figure 8:
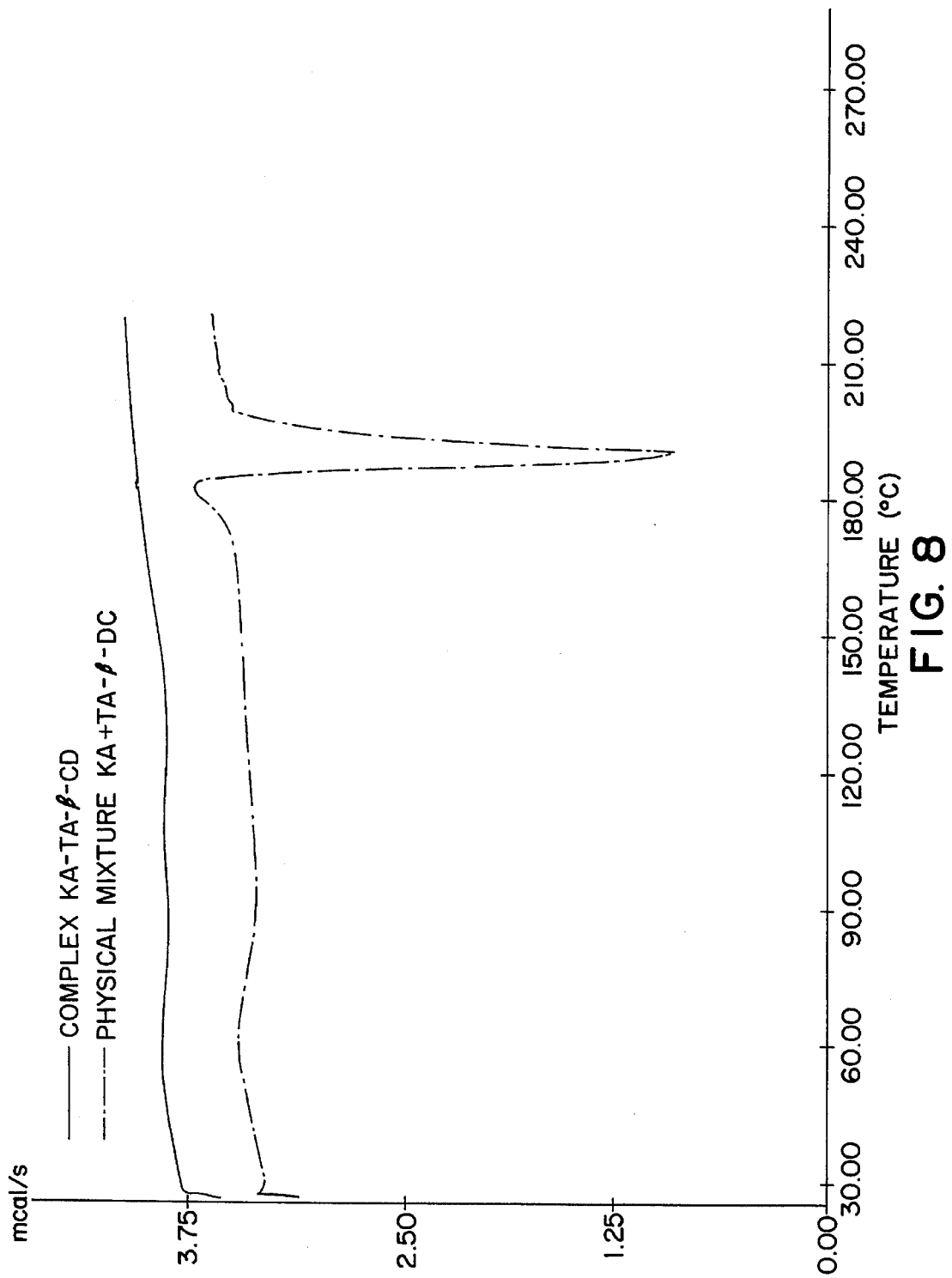

FIGS. 7 and 8 illustrate NMR and DSC spectra of the inclusion complex of clavulanic acid with triacetyl-β-CD.

EXAMPLE 5

Preparation of the inclusion complex of potassium clavulanate with methyl-β-cyclodextrin (Me-β-CD) by recomplexing from the inclusion complex of clavulanic acid with triacetyl-β-CD The inclusion complex (100 g) of clavulanic acid with heptakis-(2,3,6-tri-O-acetyl)-β-CD, which was prepared in the same way as in Example 4, was suspended in a 3% aqueous potassium carbonate solution (200 ml), in which methyl-β-CD (53.6 g, 40.9 mmol) was dissolved. The suspension was stirred for 5 min at ambient temperature, the solid particles were filtered off and the filtrate was frozen in liquid nitrogen and then freeze-dried. There was obtained a yellowish microcrystalline inclusion complex (56.7 g, 91.9%) of potassium clavulanate with methyl-β-CD. The complex contained 14.9% of potassium clavulanate as it was determined by the HPLC method.

In the same manner inclusion complexes of other alkali clavulanates can be prepared.

EXAMPLE 6

Stability test of complexed and uncomplexed potassium clavulanate in artificial gastric juice (pH 1.2) at the temperature of 37° C.

For the test the following samples were used:
1) potassium clavulanate (abbr. KK)
2) inclusion complex of KK with methyl-β-CD (abbr. KK-Me-β-CD)
3) inclusion complex of KK with 2-hydroxypropyl-β-CD (abbr. KK-HP-β-CD)
4) inclusion complex of clavulanic acid with triacetyl-β-CD (abbr. KA-TA-β-CD).

Medium: artificial gastric juice—aq. HCl/NaCl buffer, pH 1.2, according to USP XXII.
Concentration of clavulanic acid (abbr. KA) in samples: 4 mg/ml.

The samples 1 to 3 were dissolved under stirring in an artificial gastric juice (100 ml) thermostated at 37° C., at the concentration of 4 mg/ml with regard to the clavulanic acid. Subsequently, 100 μl aliquots were taken at 5 min intervals for analysis by the HPLC, until a more than 95% KA decomposition was found. The solution was stirred all the time at the temperature of 37° C. ±0.5° C.

Separately, a series of ten 10 ml aliquots of KA-TA-β-CD suspension in a buffer of a pH of 1.2 (conc. of KA=4 mg/ml), which were constantly stirred during thermostating at 37° C., was prepared. At time intervals of 5 to 10 min, the individual aliquots were filtered (membrane filter 0.4 μm) and in the clear filtrate the concentration of clavulanic acid was determined by HPLC. The KA content at times up to 90 min of thermostating was noted.

The results of measurements after 15, 30, 45, 60 and 90 min of thermostating the samples at 37° C. in a buffer at pH 1.2 are shown in following Table.

| Thermostating time [min] | KA (undecomp.) as to the initial KA conc.(100%) in samples [%] | | | Released and undecomp. KA in supernatant above suspension [%] |
| --- | --- | --- | --- | --- |
| | KK | KK-Me-β-CD | KK-HP-β-CD | KA-TA-β-CD |
| 15 min | 18.1 | 26.6 | 24.7 | 9.6 |
| 30 min | 1.3 | 11.2 | 10.2 | 10.9 |
| 45 min | 0 | 4.1 | 3.4 | 10.5 |
| 60 min | | | | 11.0 |
| 90 min | | | | 10.6 |

Figure 9:
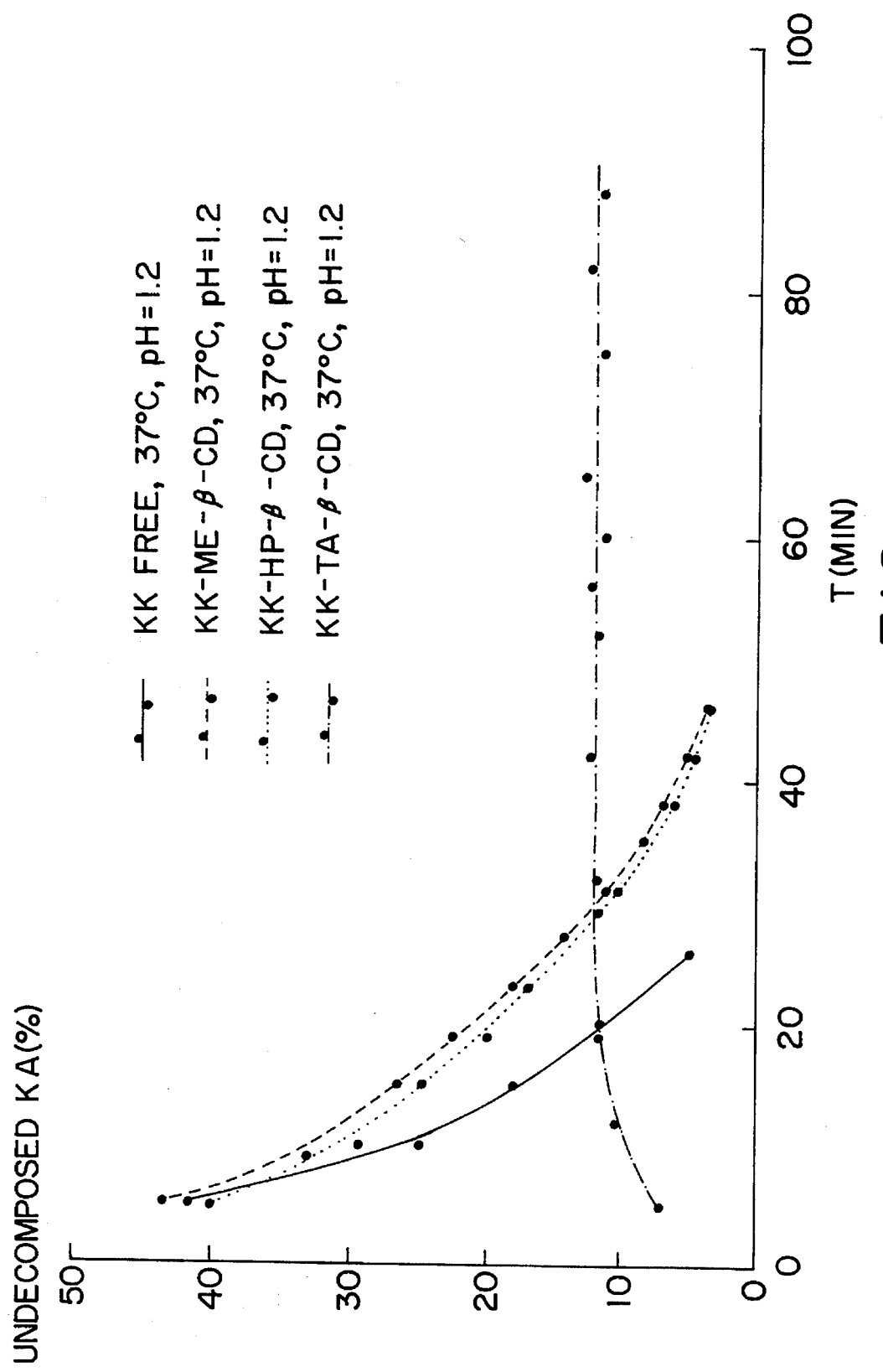

In FIG. 9, the times of 95% decomposition of clavulanic acid ($t_{95}$) are shown:

| $t_{95\%}$: | KK | 26 min |
| | KK-Me-β-CD | 42 min |
| | KK-HP-β-CD | 40 min |
| | KA-TA-β-CD | >90 min |

From the obtained results it is evident that the complexing of potassium clavulanate with hydrophilic Me-β-CD and HP-β-CD substantially increases the stability of potassium clavulanate and clavulanic acid in artificial gastric juice (pH 1.2, 37° C.). The ratio in undecomposed clavulanic acid after 30 min. is about 1:8 in the favour of complexed potassium clavulanate (see FIG. 9).

It is further evident from Diagram 1 that within 90 minutes the KA concentration in the supernatant above suspension of hydrophobic inclusion complex KA-TA-β-CD keeps constant (it contains 10 to 11% of the starting KA), which represents a sustained and constant release of KA from the complex. The decomposed clavulanic acid is simultaneuosly replaced by a new amount of clavulanic acid from the complex KA-TA-β-CD as a result of the concentration equilibrium of complexed and uncomplexed clavulanic acid. Such a profile of the release of clavulanic acid points to the applicability of the complexes of clavulanic acid with hydrophobic β-CD derivatives for sustained release forms.

After 10 minutes, a 90 ml aliquot of KA-TA-β-CD suspension was filtered and the precipitate was washed out with 10 ml of fresh buffer according to the USP XXII. Subsequently, the precipitate was quantitatively transferred to a 10 ml measuring flask, dissolved in a mixture of MeOH:H$_2$O=1:1 and filled with the solvent up to the mark. By the HPLC analysis it was determined that the sample contained 0.76 mg of KA/ml, which is 19% of the starting KA amount in the complex. These results show that from the complex KA-TA-β-CD the KA is released constantly and in a sustained manner.

The complexed part of clavulanic acid remained stable in acidic medium and the slow release at simultaneous absorption from the stomach to blood made possible a substantially greater extent of absorption than other hitherto known forms.

There was also determined the release of clavulanic acid or its potassium salt from the complex with hydrophobic triacetyl-β-CD in artificial intestinal juice (pH 7.2, buffer according to the USP XXII), which also ran constantly and about twice faster than in artificial gastric juice with pH 1.2.

From the above discussion it may be concluded that the inclusion complex of clavulanic acid with triacetyl-β-CD is a suitable sustained release system for peroral forms.

EXAMPLE 7

X-ray powder diffraction

In the Table below there are shown the lattice distances d(nm) and intensity (I) of X-ray powder diffraction patterns of potassium clavulanate (abbr. KK), methyl-β-CD (abbr. Me-β-CD), 2-hydroxypropyl-β-CD (HP-β-CD), 2-hydroxyethyl-β-CD (abbr. HE-β-CD) and of the inclusion complexes of potassium clavulanate with the enumerated β-CD derivatives (abbr. KK-ME-β-CD, KK-HP-β-CD and KK-HE-β-CD), which were taken by Philips PW 1710 diffractometer on an Al-substrate and at λ=0.15418 nm (CuKα).

| Sample | d(nm) | (I) |
| --- | --- | --- |
| KK | 0.35389 | 1694 |
| | 0.29359 | 1426 |
| | 0.37586 | 1176 |
| ME-β-CD | 0.49695 | 1454 |
| | 0.46853 | 1422 |
| | 0.49081 | 1404 |
| KK-Me-β-CD | 0.46426 | 1100 |
| | 0.49217 | 1072 |
| | 0.47133 | 1068 |
| HP-β-CD | 0.48196 | 1576 |
| | 0.46370 | 1538 |
| | 0.48650 | 1532 |
| KK-HP-β-CD | 0.46018 | 1198 |
| | 0.45376 | 1164 |
| | 0.47544 | 1140 |
| HE-β-CD | 0.47459 | 1432 |
| | 0.46811 | 1360 |
| | 0.35968 | 1298 |
| KK-HE-β-CD | 0.45327 | 1046 |
| | 0.44711 | 1018 |
| | 0.47514 | 1018 |

EXAMPLE 8

Process for the isolation of clavulanic acid or of potassium salt thereof

To an ethylacetate solution (1 l) of the inclusion complex of clavulanic acid with heptakis-(2,3,6-tri-O-acetyl)-β-CD (the concentration of clavulanic acid was 10 mg/ml as determined by the HPLC method), which was obtained according to the process of Example 4, N,N'-diisopropylethylenediamine (5 ml) was slowly added dropwise under vigorous stirring within 10 min. The resulting suspension was stirred for another 30 min, the produced precipitate was filtered off and then dissolved in 10 ml of water. Acetone (200 ml) was added to the solution, whereat N,N' -diisopropyl- ethylenediammonium diclavulanate (6.1 g) was separated in the form of fine crystalls, which were filtered off and redissolved in water (5 ml). Isopropanol (95 ml) was added to the solution and then a solution of potassium 2-ethylhexanoate (10 ml, 2M) in isopropanol was slowly added dropwise under vigorous stirring within 15 min, whereat potassium clavulanate was separated, which was filtered off, washed with isopropanol (3×10 ml) and dried in vacuum at a temperature up to 35° C. to constant weight. Thus there was obtained potassium clavulanate (2.64 g, 77%) (USP grade, clavulanic acid content 82.8% as determined by HPLC method).

EXAMPLE 9

Preparation of inclusion complex of potassium clavulanate with triacetyl-β-cyclodextrin Potassium clavulanate (237.3 mg, 1 mmol) was dissolved in water for injections (10 ml) under stirring at ambient temperature and then a solution of triacetyl-β-cyclodextrin (TA-β-CD; 2.02 g, 1 mmol) in isopropanol (90 ml) was added. The reaction mixture was stirred for 5 min at ambient temperature, subsequently the solvents was evaporated at reduced pressure, at first on a rotary evaporator at the temperature of 30° C. and then the residue was frozen and freeze-dried. Microcrystalline title complex (2.25 g, 99%) was obtained. The complex contained 9.1% of potassium clavulanate (corresponding to 0.9 mol of potassium clavulanate/1 mol of triacetyl-β-CD) as determined by the HPLC method.

The DSC analysis corresponded to the title complex.

The NMR spectrum corresponded to potassium clavulanate and triacetyl-β-CD.

EXAMPLE 10

Dispersion tablets containing clavulanic acid (125 mg) and amoxicillin (500 mg)

| Ingredients | mg/tablet | | % |
|---|---|---|---|
| inclusion complex of potassium clavulanate with Me-β-CD | 833.3 | | 27.78 |
| amoxicillin trihydrate (corresponding to 500 mg of anhydrous amoxicillin) | 574.0 | | 19.13 |
| crospovidone (Kollidon CL) | 50.0 | | 1.67 |
| saccharin | 10.0 | | 0.33 |
| flavourings (fruit) | 35.0 | | 1.17 |
| magnesium stearate | 21.0 | | 0.70 |
| colloidal silica (Aerosil 200) | 10.0 | | 0.33 |
| microcrystalline cellulose (Avicel pH 101) | ad | 3000.0 ad | 100.00 |

The equivalents of amoxicillin and clavulanic acid were mixed homogeneously and then briquetted with a part of the filler (microcrystalline cellulose). The briquettes were crushed and sieved through an oscillation sieve with a mesh size of 1.5 mm. The obtained granulate was mixed with the remaining adjuvants and tableted on a rotary tableting machine.

The tablets rapidly disintegrate in water giving a fine dispersion suitable for therapeutic application.

EXAMPLE 11

Chewing tablets containing clavulanic acid (125 mg) and amoxicillin (500 mg)

| Ingredients | mg/tablet | | % |
|---|---|---|---|
| inclusion complex of potassium clavulanate with Me-β-CD | 833.3 | | 27.78 |
| amoxicillin trihydrate (corresponding to 500 mg of anhydrous amoxicillin) | 574.0 | | 19.13 |
| crospovidone (Kollidon CL) | 5.0 | | 0.17 |
| polyvinyl pyrrolidone | 60.0 | | 2.00 |
| colloidal silica (Aerosil 200) | 10.0 | | 0.33 |
| saccharin | 10.0 | | 0.33 |
| flavourings (fruit) | 35.0 | | 1.17 |
| magnesium stearate | 15.0 | | 0.50 |
| microcrystalline cellulose (Avicel pH 101) | 60.0 | | 2.00 |
| mannitol | ad | 3000.0 ad | 100.00 |

The equivalents of amoxicillin and clavulanic acid were homogeneously mixed together with a part of the fillers (microcrystalline cellulose and mannitol) and the obtained mixture of powders was briquetted. The briquettes were crushed and sieved through an oscillation sieve with a mesh size of 1.5 mm. The obtained granulate was mixed with the remaining adjuvants and tableted.

Tablets were suitable for chewing.

We claim:

1. A process for the preparation of clavulanic acid or of potassium salt thereof from a concentrate of a clear aqueous solution of crude clavulanic acid in the form of a sodium salt obtained after the fermentation with a clavulanic-acid-producing microorganism, which is acidified with sulfuric acid to a pH value between 1 and 3, wherein acidified solution of crude clavulanic acid is immediately extracted with a solution of a hydrophobic β-cyclodextrin derivative selected from the group consisting of heptakis-(2,3,6-tri-O-acetyl)-β-cyclodextrin, heptakis-(2,6-di-O-ethyl)-β-cyclodextrin, heptakis-(2,3-di-O-ethyl)-β-cyclodextrin and heptakis-(2,3,6-tri-O-ethyl)-β-cyclodextrin in an inert organic solvent, the so formed crude intermediate inclusion complex of clavulanic acid with said hydrophobic β-cyclodextrin is isolated from the organic phase, subsequently purified with water and the purified said inclusion complex is then converted with potassium 2-ethyl hexanoate to potassium clavulanate, which is then isolated.

2. A process for the preparation of clavulanic acid or of potassium salt thereof according to claim 1, wherein acidified solution of crude clavulanic acid is extracted with a solution of heptakis-(2,3,6-tri-O-acetyl)-β-CD in ethyl acetate as the inert organic solvent to form an inclusion complex of clavulanic acid with heptakis-(2,3,6-tri-O-acetyl)-β-CD.

3. A process for the preparation of clavulanic acid or of potassium salt thereof according to claim 1, wherein the intermediate inclusion complex of clavulanic acid with heptakis-(2,3,6-tri-O-acetyl)-β-CD is converted with potassium 2-ethyl hexanoate to potassium clavulanate.

4. A process for the preparation of clavulanic acid or of potassium salt thereof according to claim 1, the intermediate inclusion complex of clavulanic acid with said hydrophobic-β-cyclodextrin is formed in a molar ratio of about 1:1.

5. A process for the preparation or clavulanic acid or of potassium salt thereof according to claim 1, wherein the intermediate inclusion complex of clavulanic acid with heptakis-(2,3,6-tri-O-acetyl)-β-cyclodextrin is formed in a molar ratio of about 1:1.

6. A process for the preparation of the potassium salt of clavulanic acid according to claim 1 wherein said inclusion complex is converted with potassium 2-ethyl hexanoate.

* * * * *

UNITED STATES PATENT AND TRADEMARK OFFICE
CERTIFICATE OF CORRECTION

PATENT NO. : 5,498,788
DATED : March 12, 1996
INVENTOR(S) : Zmitek et al.

It is certified that error appears in the above-indentified patent and that said Letters Patent is hereby corrected as shown below:

On the title page item [57],

Line 1, please change "alkali" to ---pure clavulanic acid and of pharmaceutically acceptable potassium---.

Line 2, cancel "pure" and insert ---crude---.

Cancel line 3.

Line 4, cancel "lanic acid"

Signed and Sealed this

Fifteenth Day of October, 1996

Attest:

BRUCE LEHMAN

Attesting Officer     Commissioner of Patents and Trademarks